(12) United States Patent
Nishide et al.

(10) Patent No.: US 8,900,727 B2
(45) Date of Patent: Dec. 2, 2014

(54) CONDENSED POLYCYCLIC COMPOUND, ORGANIC LIGHT-EMITTING DEVICE HAVING THE SAME, DISPLAY DEVICE, IMAGE INFORMATION PROCESSING DEVICE, LIGHTING DEVICE, IMAGE FORMATION DEVICE, AND EXPOSURE LIGHT SOURCE

(75) Inventors: Yosuke Nishide, Kawasaki (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 13/594,549

(22) Filed: Aug. 24, 2012

(65) Prior Publication Data

US 2013/0050561 A1 Feb. 28, 2013

(30) Foreign Application Priority Data

Aug. 29, 2011 (JP) .................. 2011-186205

(51) Int. Cl.
*C07C 13/62* (2006.01)
*H01L 51/54* (2006.01)
(Continued)

(52) U.S. Cl.
CPC . *C07C 13/62* (2013.01); *C09B 3/14* (2013.01); *G09G 3/3208* (2013.01); *C07C 25/22* (2013.01); *H05B 33/14* (2013.01); *H01L 51/0056* (2013.01); *C07C 2103/54* (2013.01); *H01L 51/5012* (2013.01); *H04N 5/225* (2013.01); *C09B 3/00* (2013.01); *C09B 1/00* (2013.01); *Y10S 428/917* (2013.01)
USPC .......... 428/690; 428/917; 313/504; 313/506; 348/335; 585/27; 345/82

(58) Field of Classification Search
None
See application file for complete search history.

(56) References Cited

U.S. PATENT DOCUMENTS

2002/0168544 A1* 11/2002 Fukuoka et al. ............... 428/690
2003/0137241 A1* 7/2003 Fujita et al. ................... 313/504
(Continued)

FOREIGN PATENT DOCUMENTS

JP 10-330295 A 12/1998

*Primary Examiner* — Dawn L. Garrett
(74) *Attorney, Agent, or Firm* — Canon U.S.A., Inc. IP Division

(57) ABSTRACT

A condensed polycyclic compound represented by the following general formula [1],

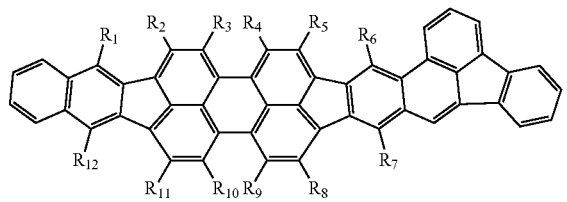

wherein, in General Formula [1], $R_1$, $R_6$, $R_7$, and $R_{12}$ each are independently selected from a hydrogen atom, an alkyl group, or an aryl group, the aryl group may have an alkyl group and a fluorine atom as a substituent, and $R_2$ to $R_5$ and $R_8$ to $R_{11}$ each are independently selected from a hydrogen atom and an alkyl group.

11 Claims, 1 Drawing Sheet

(51) Int. Cl.
    G09G 3/32      (2006.01)
    H04N 5/225     (2006.01)
    C09B 3/14      (2006.01)
    C07C 25/22     (2006.01)
    H05B 33/14     (2006.01)
    H01L 51/00     (2006.01)
    H01L 51/50     (2006.01)
    C09B 3/00      (2006.01)
    C09B 1/00      (2006.01)

(56)          References Cited

U.S. PATENT DOCUMENTS

2004/0076853  A1*   4/2004   Jarikov .................. 428/690
    2005/0054852  A1*   3/2005   Fujita et al. ............. 546/37

* cited by examiner

CONDENSED POLYCYCLIC COMPOUND, ORGANIC LIGHT-EMITTING DEVICE HAVING THE SAME, DISPLAY DEVICE, IMAGE INFORMATION PROCESSING DEVICE, LIGHTING DEVICE, IMAGE FORMATION DEVICE, AND EXPOSURE LIGHT SOURCE

BACKGROUND OF THE INVENTION

1. Field of the Invention

The present invention relates to a novel condensed polycyclic compound, an organic light-emitting device having the same, a display device, an image information processing device, a lighting device, an image formation device, and an exposure light source.

2. Description of the Related Art

Organic light-emitting devices are devices each having a pair of electrodes and an organic compound layer disposed therebetween. By injecting electrons and holes from the pair of electrodes, excitons of a light-emitting organic compound in the organic compound layer are generated, and light is emitted when the excitons return to the ground state.

The organic light-emitting devices are referred to as "organic electroluminescence devices" or "organic EL devices". A recent progress of the organic light-emitting devices is remarkable, which allows the formation of thin and lightweight light-emitting devices having high luminance at a low applied voltage, diversity in light emission wavelengths, and rapid response.

The creation of a novel organic compound which emits red light has been actively performed until now. However, in providing an organic light-emitting device having higher color purity and higher efficiency, the creation of the above-described compound has been required.

Japanese Patent Laid-Open No. 10-330295 discloses a condensed polycyclic compound a-1 as a red light-emitting material.

Although the condensed polycyclic compound a-1 described in Japanese Patent Laid-Open No. 10-330295 emits light in the red light emission region, the luminous efficiency and the color purity are not sufficient.

SUMMARY OF THE INVENTION

Aspects of the present invention provide a novel condensed polycyclic compound which emits red light with high color purity and a high emission quantum yield and has high electron injecting properties.

Aspects of the present invention provide a novel condensed polycyclic compound represented by the following general formula [1].

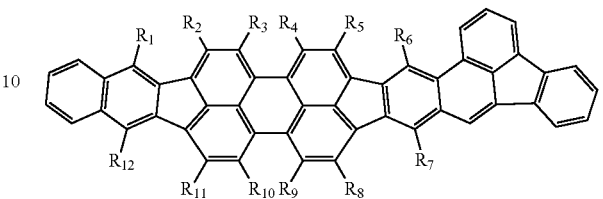

[1]

In General Formula [1], $R_1$, $R_6$, $R_7$, and $R_{12}$ each are independently selected from a hydrogen atom, an alkyl group, or an aryl group.

The aryl group may have an alkyl group and a fluorine atom as a substituent.

$R_2$ to $R_5$ and $R_8$ to $R_{11}$ each are independently selected from a hydrogen atom and an alkyl group.

Aspects of the invention can provide a novel condensed polycyclic compound which emits red light with high color purity and a high emission quantum yield and which has high electron injection properties. Aspects of the invention also provide a red organic light-emitting device which has the novel condensed polycyclic compound and has high color purity and high efficiency.

Further features of the present invention will become apparent from the following description of exemplary embodiments with reference to the attached drawings.

DESCRIPTION OF THE EMBODIMENTS

Figure 1:
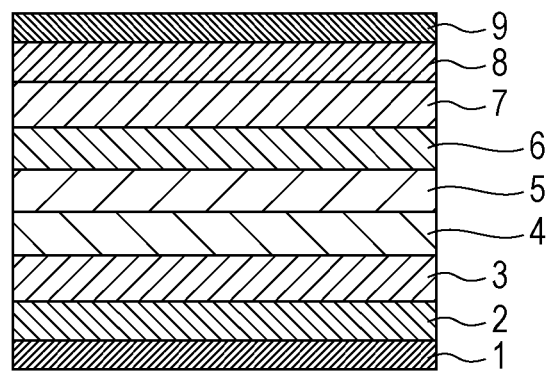
FIG. 1 is a schematic view of an example of a laminated type organic light-emitting device according to this embodiment.

Aspects of the invention include a novel condensed polycyclic compound represented by the following general formula [1].

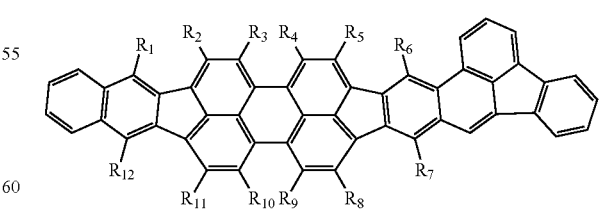

[1]

In General Formula [1], $R_1$, $R_6$, $R_7$, and $R_{12}$ each are independently selected from a hydrogen atom, an alkyl group, or an aryl group.

The aryl group may have an alkyl group and a fluorine atom as a substituent.

The alkyl group of the aryl group is suitably an alkyl group having carbon atoms of 1 or more and 4 or lower and is particularly suitably a methyl group, an ethyl group, an iso-propyl group, and a t-butyl group.

$R_2$ to $R_5$ and $R_8$ to $R_{11}$ each are independently selected from a hydrogen atom and an alkyl group. The alkyl groups at $R_1$, $R_6$, $R_7$, and $R_{12}$ are suitably alkyl groups having carbon atoms of 1 or more and 4 or lower.

The aryl groups at $R_1$, $R_6$, $R_7$, and $R_{12}$ are suitably a phenyl group, a biphenyl group, and a terphenyl group and particularly suitably phenyl groups.

The alkyl groups at $R_2$ to $R_5$ and $R_8$ to $R_{11}$ are suitably alkyl groups having carbon atoms of 1 or more and 4 or lower and are particularly suitably a methyl group, an ethyl group, and an iso-propyl group.

The novel condensed polycyclic compound according to aspects of the invention emits red light with high color purity and a high quantum yield and has a low LUMO.

Therefore, when the compound according to aspects of the invention is used as a light-emitting material of the organic light-emitting device, the electron injection properties are improved, so that the luminous efficiency of the organic light-emitting device is high.

Herein, the fact that the LUMO becomes low is the same as the fact that the LUMO value becomes small. Moreover, "The LUMO is low." can be expressed by "The LUMO is shallow".

Therefore, a red organic light-emitting device having high efficiency and high color purity can be provided by containing the compound according to aspects of the invention.

Comparison of Exemplary Compound A1 According to Aspects of Invention and Condensed Polycyclic Compound a-1

An exemplary compound A1 according to aspects of the invention and a condensed polycyclic compound a-1 described in Japanese Patent Laid-Open No. 10-330295 are compared and described.

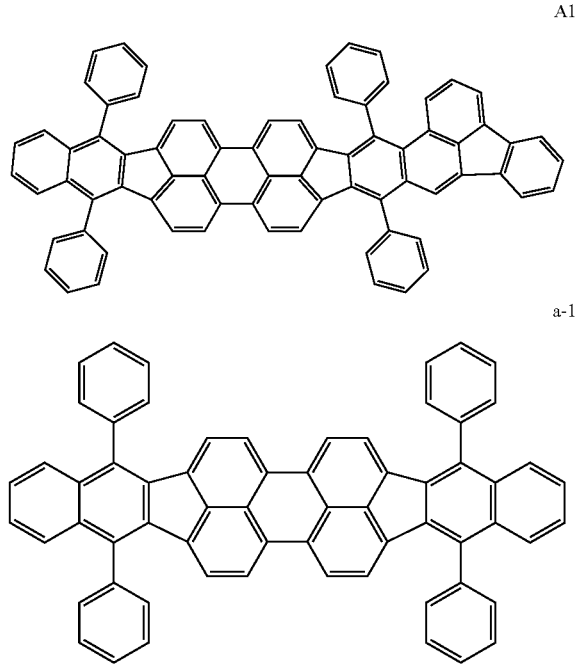

A1 a-1

Both the condensed polycyclic compound A1 according to aspects of the invention and the condensed polycyclic compound a-1 described in Japanese Patent Laid-Open No. 10-330295 have light emission in the red light emission region.

When the emission spectra of the condensed polycyclic compound A1 according to aspects of the invention and the condensed polycyclic compound a-1 were measured similarly as in the method described in Example 1, the peak wavelengths thereof were 606 nm and 597 nm, respectively.

The light emission in the red light emission region in this embodiment refers to light emission in a region in which the peak wavelength of the emission spectrum in a toluene diluted solution is 580 nm or more and 630 nm or lower.

The red light emission with high color purity is suitably one in a light emission region of 600 nm or more and 620 nm or lower.

Since the condensed polycyclic compound A1 and other exemplary compounds according to aspects of the invention emit light in a region of 600 nm or more and 630 nm or lower, red light emission with higher color purity than that of the light emission from the condensed polycyclic compound a-1 can be achieved.

The emission quantum yield of the condensed polycyclic compound A1 according to aspects of the invention is approximately 1.3 times higher than that of the condensed polycyclic compound a-1.

When the emission quantum yield in the toluene diluted solution was measured, the emission quantum yield of the exemplary compound A1 according to the invention was 0.79 and the emission quantum yield of the condensed polycyclic compound a-1 was 0.62.

This is because, in the condensed polycyclic compound according to aspects of the invention, the effective conjugation length of molecules is large in the axial direction of the base skeleton and the transition dipole moment is large.

Therefore, when the condensed polycyclic compound A1 according to aspects of the invention is used for the organic light-emitting device, light emission with higher efficiency than that of the light emission from the condensed polycyclic compound a-1 can be obtained.

Moreover, since the LUMO of the condensed polycyclic compound A1 according to aspects of the invention is lower than that of the condensed polycyclic compound a-1, the electron injection properties are high.

The condensed polycyclic compound A1 according to aspects of the invention has three 5-membered rings at the fluoranthene site in the molecules. In contrast, the condensed polycyclic compound a-1 has only two 5-membered rings at the fluoranthene site in the molecules.

Since the 5-membered ring at the fluoranthene site lacks electrons, the electron acceptability becomes high and the LUMO becomes low.

Thus, the condensed polycyclic compound A1 according to aspects of the invention in which the number of the 5-membered rings is larger has higher electron acceptability and a lower LUMO.

When a compound having a low LUMO is used for the light-emitting material of the organic light-emitting device, a reduction in the drive voltage of the device can be expected due to high electron injection properties to the light-emitting material. Moreover, since electrons are confined in a light-emitting layer, an increase in efficiency and an extension of life-span can be achieved.

When the condensed polycyclic compound A1 according to aspects of the invention and the condensed polycyclic compound a-1 were subjected to molecular orbital calculation by the following method, it was found that the calculated value of LUMO also suggested the above-described fact.

Therefore, when the exemplary compound A1 according to aspects of the invention is used for the organic light-emitting device, light emission with longer life and higher efficiency can be obtained at a lower voltage than those of the light emission from the condensed polycyclic compound a-1.

As described above, the condensed polycyclic compound A1 having a high quantum yield electron and high electron injection properties according to aspects of the invention can provide an organic light-emitting device in which the voltage is further lowered, the life span is further extended, and the efficiency is further increased than that obtained by the condensed polycyclic compound a-1.

The novel condensed polycyclic compound according to aspects of the invention can be suitably used for the light-emitting material of the organic light-emitting device.

In the above description, the condensed polycyclic compound A1 according to aspects of the invention is compared as an example. Since three 5-membered rings are present in the molecules in according to aspects of the invention, it is considered that the above-described characteristics apply to all the novel condensed polycyclic compounds according to aspects of the invention.

TABLE 1

| Compound | Molecular structural formula | LUMO (eV) |
| --- | --- | --- |
| A1 | | −2.47 |
| B1 | | −2.53 |
| C1 | | −2.51 |
| a-1 | | −2.37 |

The molecular orbital calculation was performed using the quantum chemical calculation method described below.

In the molecular orbital calculation, LUMO was determined using the following technique.

For the molecular orbital calculation described above, the calculation technique of DFT basis function 6–31+G (d) was used employing Gaussian 03, which is widely used at present, (Gaussian 03, Revision D. 01, M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004).

Examples of Organic Compound According to Aspects of Invention

Specific examples of the condensed polycyclic compound according to aspects of the invention are shown below. However, the invention is not limited thereto.

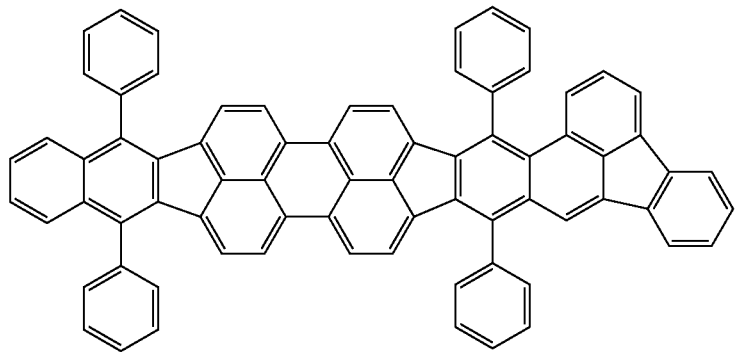

A1

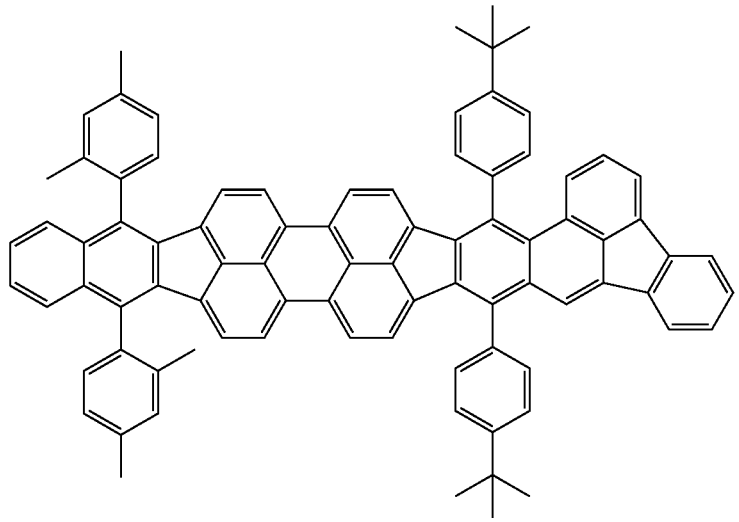

A2

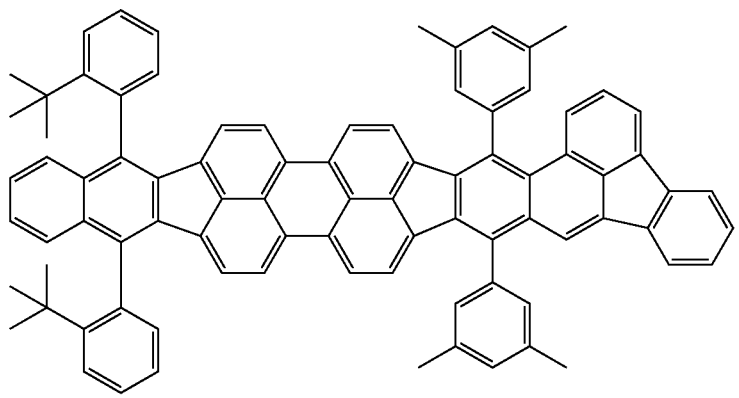

A3

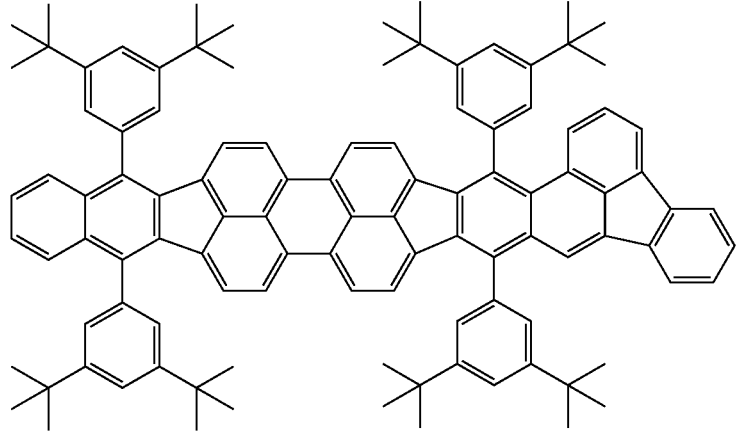
A4
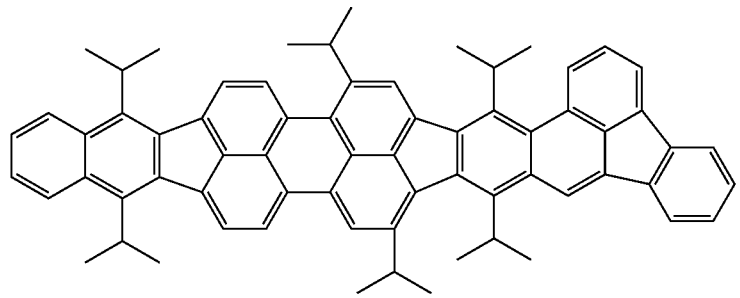
B1
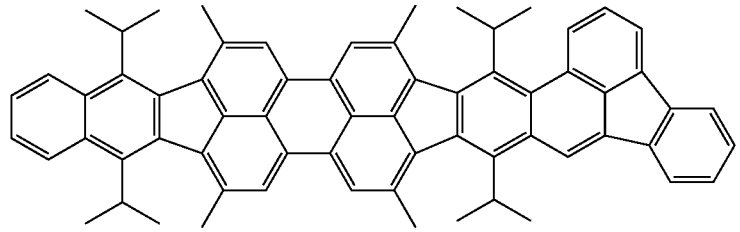
B2
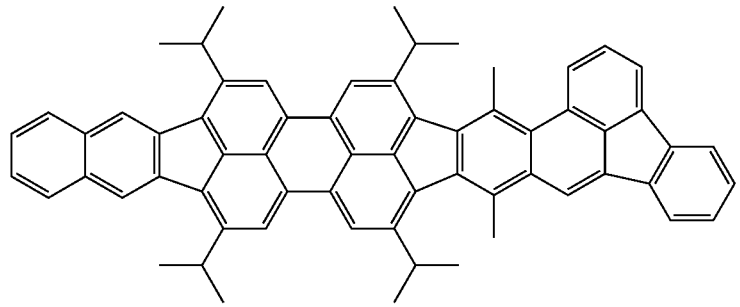
B3
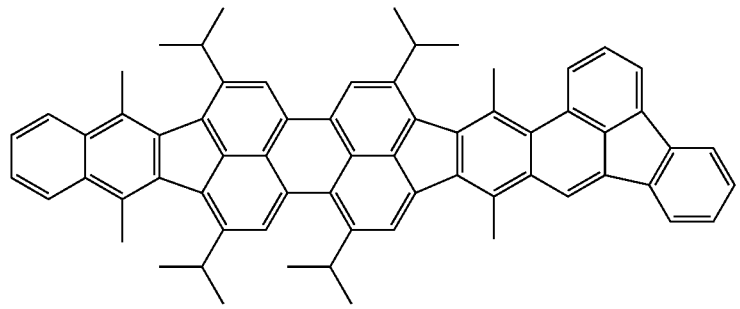
B4

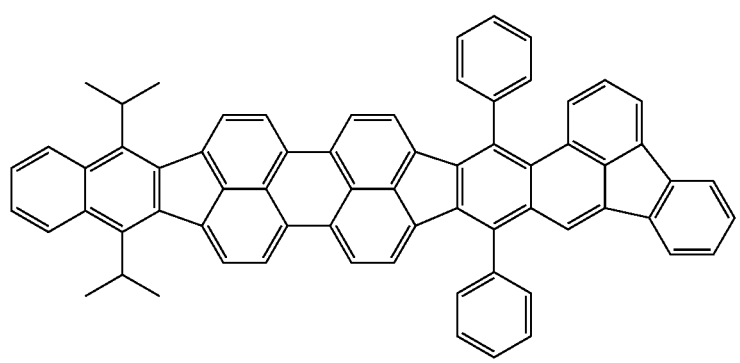
C1
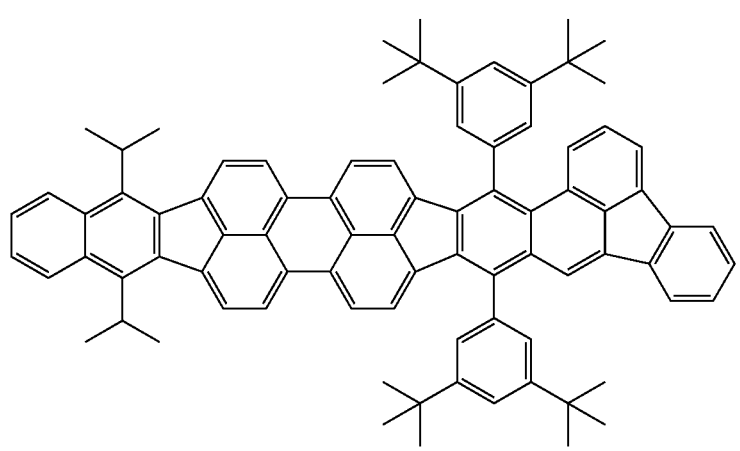
C2
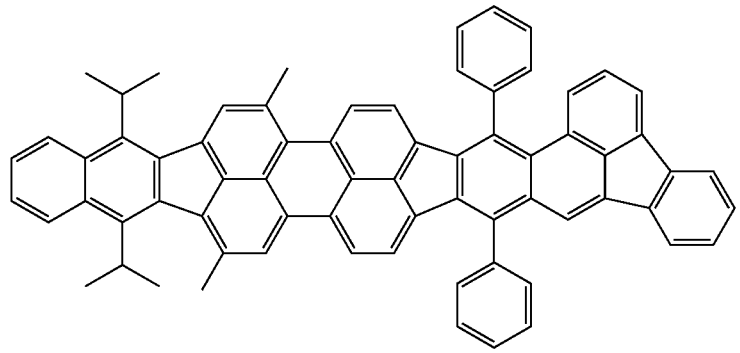
C3
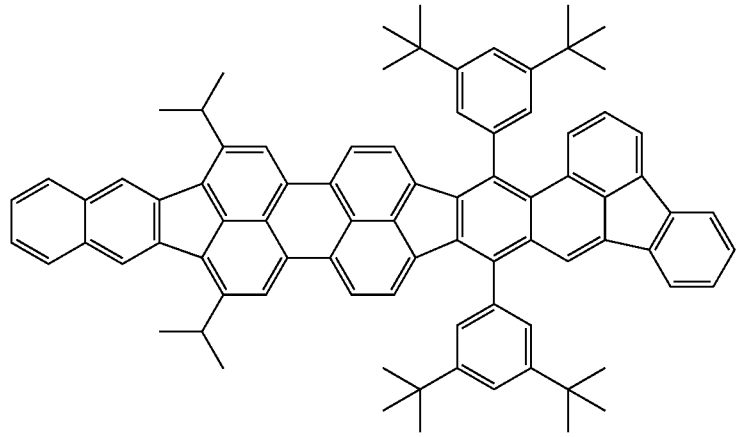
C4

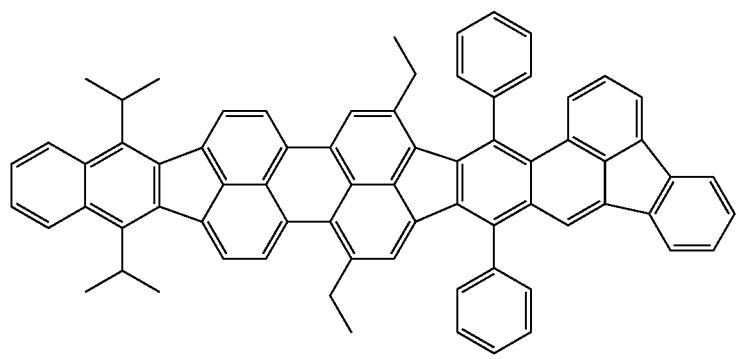
C5
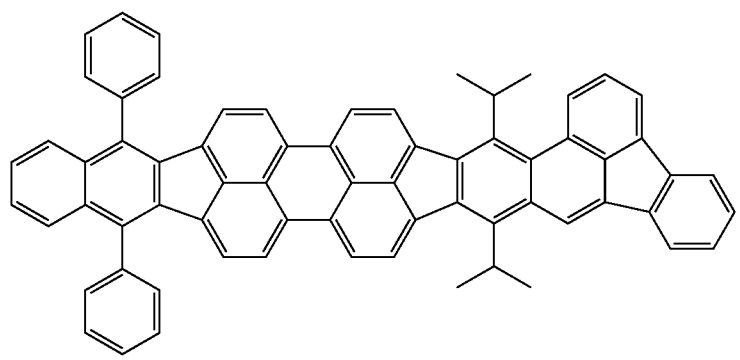
C6
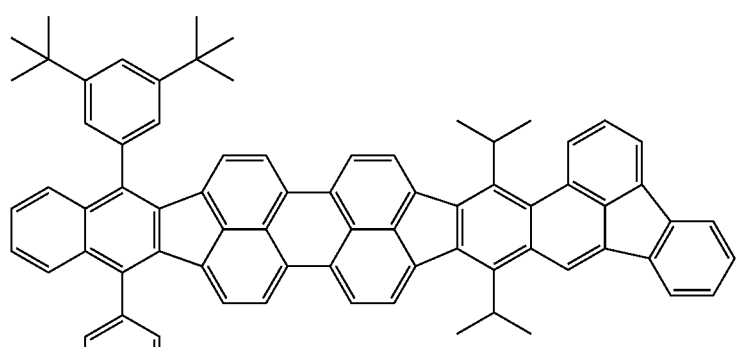
C7
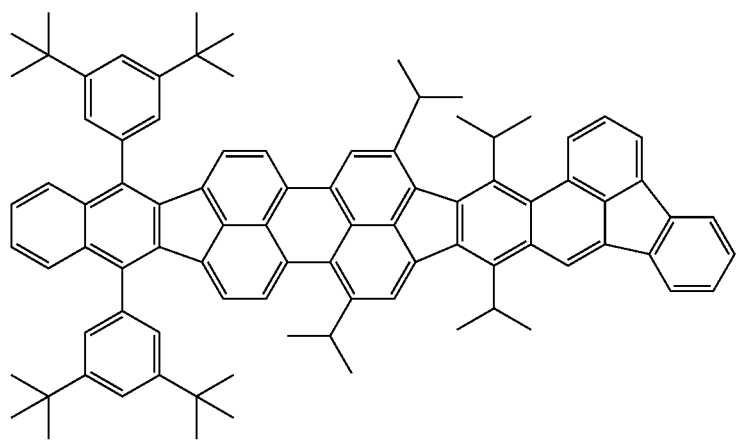
C8

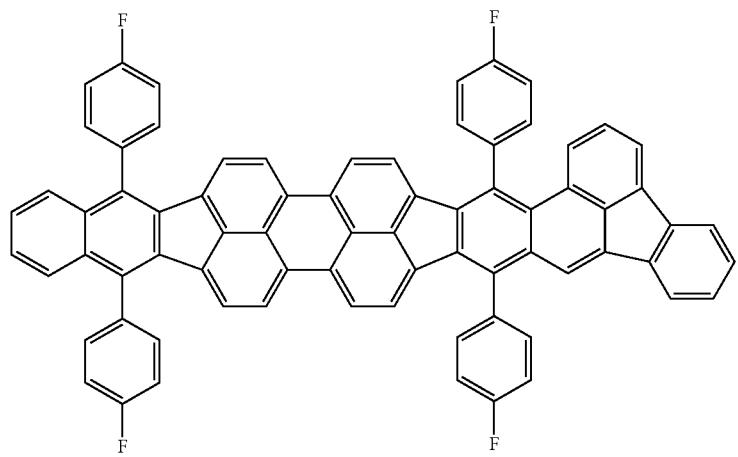
D1
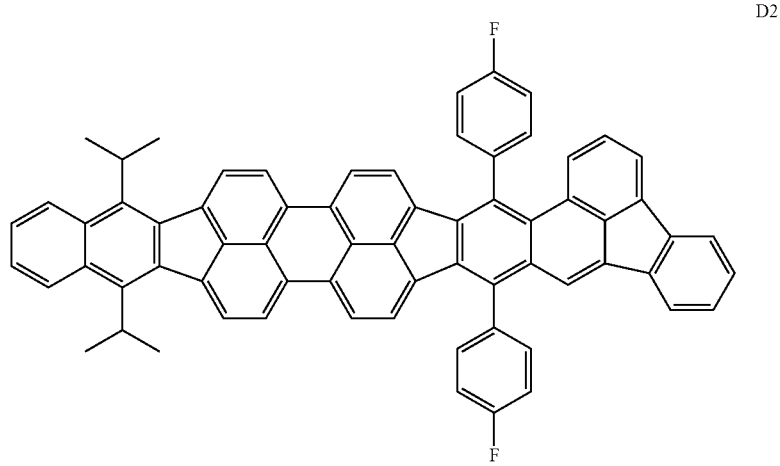
D2
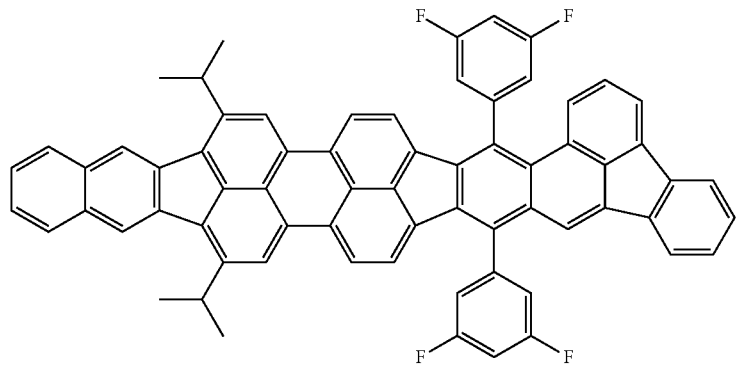
D3
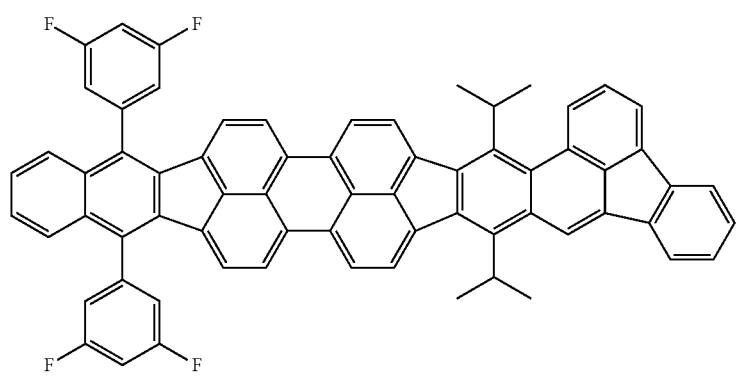
D4

Properties of Exemplary Compounds

Specific examples of the condensed polycyclic compound according to aspects of the invention are shown in Groups A to D.

In all the compounds of Groups A to D, at least any one of a methyl group, an ethyl group, an iso-propyl group, a t-butyl group, a phenyl group, and a fluoride group, is substituted.

It is performed for the purpose of suppressing the stacking and adjusting the light emission wavelength. The stacking suppressing effect becomes higher as a larger number of the substituents are provided to the basic skeleton.

The adjustment of the light emission wavelength plays an important role not only for increasing the color purity but also for combining the organic light-emitting device and a color filter.

Since all the compounds of Group A to Group C are constituted by hydrocarbons, the heat stability and the electrochemical stability are high.

During driving of the organic light-emitting device, an environment is formed in the device where Joule heat arises and oxidation-reduction is repeated in the organic compound. Therefore, the stability of the compound is an important characteristic.

Group A is a compound group in which the substituents contain only phenyl groups in General Formula [1]. The carbon-carbon bond of phenyl groups has higher bond dissociation energy than that of the carbon-carbon bond of alkyl groups.

Thus, the bond dissociation energy is higher in the case where a phenyl group is provided to the basic skeleton of the condensed polycyclic compound according to aspects of the invention than in the case where an alkyl group is provided thereto.

Therefore, the heat stability is higher in the case where the substituent provided to the basic skeleton is a phenyl group than in the case where the substituent is an alkyl group. Thus, Group A in which the substituents contain only phenyl groups has the highest heat stability among the condensed polycyclic compounds according to aspects of the invention.

Group B is a compound group in which the substituents contain only alkyl groups in General Formula [1]. The molecular weight of alkyl groups shown in Group B is lower than that of aryl groups. Thus, the sublimation temperature of the compounds in which the substituents contain only alkyl groups becomes low.

Therefore, Group B is a compound group with a low sublimation temperature among the compounds according to aspects of the invention.

Group C is a compound group in which both phenyl groups and alkyl groups are provided as substituents in General Formula [1]. As described above, the heat stability of the phenyl groups is higher than that of the alkyl groups.

Furthermore, since the phenyl groups have alkyl groups, the stacking suppressing effect is high. Thus, the phenyl groups are suitable.

Group D is a compound group having a phenyl group in which a fluorine atom is substituted at any one of $R_1$, $R_6$, $R_7$, or $R_{12}$ in General Formula [1]. When a fluorine group is introduced, a reduction in stacking between molecules can be expected.

This is because the fluorine atom has very high electronegativity, and therefore large polarization occurs in the molecules, so that the distance between the molecules increases due to the electrical repulsion.

Moreover, the molecular weight of the fluorine group is smaller than that of the alkyl group and the phenyl group which suppress stacking between molecules. Therefore, the sublimation temperature of the compound in which stacking is suppressed by the fluorine atom is lower than that of the compound provided with the alkyl group.

Therefore, in Group D, the effect of suppressing stacking between molecules is high and the sublimation temperature is also low among the compounds according to aspects of the invention.

With respect to the substitution position and the type of the substituents, even when substituents, such as an aryl group and an alkyl group, are provided at substitution positions other than the substitution positions mentioned for exemplary compounds, the novel condensed polycyclic compound according to aspects of the invention achieves the same effects.

Description of Organic Light-Emitting Device

Next, the organic light-emitting device according to this embodiment is described.

The organic light-emitting device according to this embodiment is an device having an anode and a cathode which are a pair of electrodes and an organic compound layer disposed therebetween, in which the organic compound layer has the organic compound represented by General Formula [1].

The organic compound layer of the organic light-emitting device according to this embodiment may be a single layer or multiple layers. The multiple layers are layers suitably selected from a hole injecting layer, a hole transporting layer, a light-emitting layer, a hole blocking layer, an electron transporting layer, an electron injecting layer, an exciton blocking layer, and the like. It is a matter of course that a plurality of substances can be selected from the groups, and can be used in combination.

The light-emitting layer may be a single layer or multiple layers. For example, in the case of a white light-emitting device, a device is mentioned in which the organic light-emitting device has a plurality of light-emitting layer and white light is emitted as a device by the emission of lights of different colors from the light-emitting layers.

One layer of the plurality of light-emitting layers of the organic light-emitting device which emits white light according to this embodiment has the condensed polycyclic compound represented by General Formula [1]. Therefore, the layer is a light-emitting layer which emits red light.

Since the light-emitting layers other than the light-emitting layer which emits red light of the plurality of light-emitting layers emit lights of colors different from red, white light is emitted as the entire device. More specifically, it is a device which emits white light by mixing red color and other colors.

In addition thereto, when the light-emitting layer is a single layer and a plurality of light-emitting materials are compounded, white light can be emitted.

As the aspect of the organic light-emitting device which emits white light according to this embodiment, the configurations of the light-emitting layers described below are mentioned but the invention is not limited thereto.

(1) Single layer: Device containing blue, green, and red light-emitting materials; (2) Laminated layers: Device containing light blue and yellow light-emitting materials; (3) Two layers: Laminated device containing a blue light-emitting layer and a light emitting layer containing green and red light-emitting materials or a red light-emitting layer and a light-emitting layer containing blue and green light-emitting materials; (4) Two layers: Laminated device containing a light-blue light-emitting layer and a yellow light-emitting layer; and (5) Three layers: Laminated device containing a blue light-emitting layer, a green light-emitting layer, and a red light-emitting layer.

FIG. 1 is a cross-sectional schematic view illustrating an example of the configuration of a device having the light-emitting layer of the configuration (5) above as an example of the white organic light-emitting device according to this embodiment. In the drawing, an organic light-emitting device having light-emitting layers of three colors is illustrated. The details of the structure are described below.

The organic light-emitting device has a device configuration in which an anode 1, a hole injecting layer 2, a hole transporting layer 3, a blue light-emitting layer 4, a green light-emitting layer 5, a red light-emitting layer 6, an electron transporting layer 7, an electron injecting layer 8, and a cathode 9 are laminated on a substrate, such as glass. The blue, green, and red light-emitting layers may be laminated in random order.

The aspect is not limited to the aspect in which the light-emitting layers are laminated, and an aspect in which the light-emitting layers are disposed side by side may be acceptable. The state where the light-emitting layers are disposed side by side refers to a state where all of the light-emitting layers disposed side by side contact the hole transporting layer and the electron transporting layer.

Moreover, an aspect in which a domain of light-emitting layers which emit other colors is formed in a light-emitting layer which emits light of one color may be acceptable as the light-emitting layer.

At least one of the plurality of light-emitting layers has the condensed polycyclic compound according to aspects of the invention. The light-emitting layer is suitably a light-emitting layer which emits red light.

One example of the organic light-emitting device which emits white light described in this embodiment is an organic light-emitting device which emits white light by mixing colors of lights emitted from the light-emitting layers other than the light-emitting layer which emits red light among the plurality of light-emitting layers and red light.

As the plurality of light-emitting layers, a configuration may be acceptable such that a light-emitting portion has a plurality of light-emitting layers.

When obtaining an organic light-emitting device which emits white light, the blue light-emitting material is not particularly limited but a light-emitting material having a fluoranthene skeleton or an anthracene skeleton is suitable.

The green light-emitting material is not particularly limited but a light-emitting material having a fluoranthene skeleton or an anthracene skeleton is suitable.

The condensed polycyclic compound represented by General Formula [1] according to aspects of the invention can be used as a host material or a guest material of the light-emitting layer. Particularly when using the condensed polycyclic compound as the guest material, a high efficient light-emitting device is provided which emits light in the red region having a light emission peak in a region of 580 nm to 660 nm.

Although the light-emitting material of the blue light-emitting layer and the light-emitting material of the green light-emitting layer are not particularly limited, it is suitable to use a compound having a fluoranthene skeleton or an anthracene skeleton.

It can be suitably used as the guest material of the light-emitting layer. The guest material can also be referred to as a dopant material.

Herein, the host material is a material with the highest weight ratio among the compounds constituting the light-emitting layers and the guest material is a material whose weight ratio is lower than that of the host material among the compounds constituting the light-emitting layers and performs main light emission.

An assist material is a material whose weight ratio is lower than that of the host material among the compounds constituting the light-emitting layers and assists the light emission of the guest material. The assist material can also be referred to as a second host.

The condensed polycyclic compound according to aspects of the invention can be used as the guest material which emits red light. The color of light emitted from the organic light-emitting device employing the compound as the entire device is not particularly limited and red light may be emitted or white light may be emitted.

When using the condensed polycyclic compound according to this embodiment as the guest material, the concentration of the guest material to the host material is suitably 0.1% by mass or more and 30% by mass or lower and more suitably 0.5 wt % or more and 10 wt % or lower.

The condensed polycyclic compound according to aspects of the invention can also be used for the hole injecting layer. This is because the compound has high HOMO, and therefore the compound assists the injection of holes from the anode to the organic compound layer.

That fact that the HOMO of the condensed polycyclic compound according to aspects of the invention is high results from the fact that the LUMO is low and red light is emitted. Since the band gap of the compound which emits red light is small, it is understood that the HOMO of the compound is high considering the fact that the LUMO is low.

Besides the condensed polycyclic compound according to aspects of the invention, the organic light-emitting device according to this embodiment can contain known hole injectable materials or known hole transportable materials or known host materials or known guest materials, known electron injectable materials or known electron transportable materials, or the like optionally together. These materials may be low molecular weight materials or high molecular weight materials.

Examples of the compounds are mentioned below.

The hole injectable materials or the hole transportable materials are suitably materials having a high hole mobility. Mentioned as low molecular weight materials or high molecular weight materials having hole injection performance or hole transportation performance are a triarylamine derivative, a phenylenediamine derivative, a stilbene derivative, a phthalocyanine derivative, a porphyrin derivative, poly (vinylcarbazole), poly(thiophene), and other conductive polymers but it is a matter of course that the materials are not limited thereto.

Mentioned as the host materials are a triarylamine derivative, a phenylene derivative, condensed ring aromatic compounds (e.g., a naphthalene derivative, a phenanthrene derivative, a fluorene derivative, a chrysene derivative, and the like), organic metal complexes (e.g., organic aluminum complexes, such as tris(8-quinolinolato)aluminum, an organic beryllium complex, an organic iridium complex, an organic platinum complex, and the like), and high molecular weight derivatives, such as a poly(phenylenevinylene) derivative, a poly(fluorene) derivative, a poly(phenylene) derivative, a poly(thienylenevinylene) derivative, and a poly(acetylene) derivative and it is a matter of course that the host materials are not limited thereto.

As the host compounds, specific structural formulae are shown in Table 2. The host compounds may be compounds which are derivatives having structural formulae shown in Table 4. Besides the compounds, mentioned are condensed compounds (e.g., a fluorene derivative, a naphthalene derivative, an anthracene derivative, a pyrene derivative, a carbazole derivative, a quinoxaline derivative, a quinoline derivative, and the like), organic aluminum complexes, such as tris(8-quinolinolato)aluminum, an organic zinc complex, and high molecular weight derivatives, such as a triphenylamine derivative, a poly(fluorene) derivative, and a poly(phenylene) derivative and it is a matter of course that the host compounds are not limited thereto.
TABLE 2
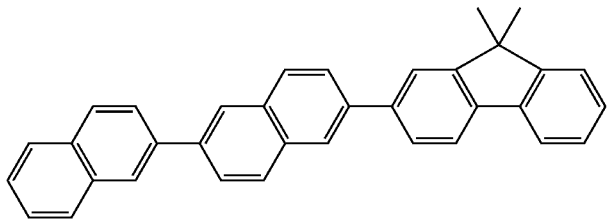 [SMILES: CC1(C)c2ccccc2-c2ccc(-c3ccc4cc(-c5ccc6ccccc6c5)ccc4c3)cc21]
H1
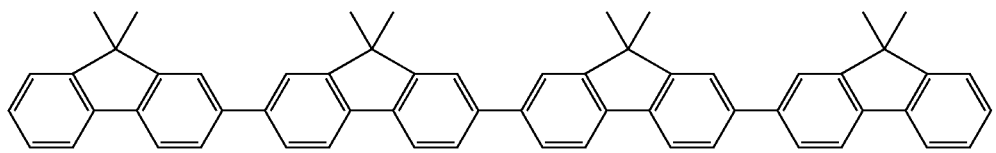 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]
H2
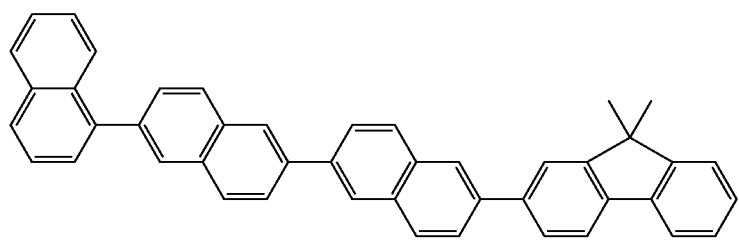 [SMILES: CC1(C)c2ccccc2-c2ccc(-c3ccc4cc(-c5ccc6cc(-c7cccc8ccccc78)ccc6c5)ccc4c3)cc21]
H3
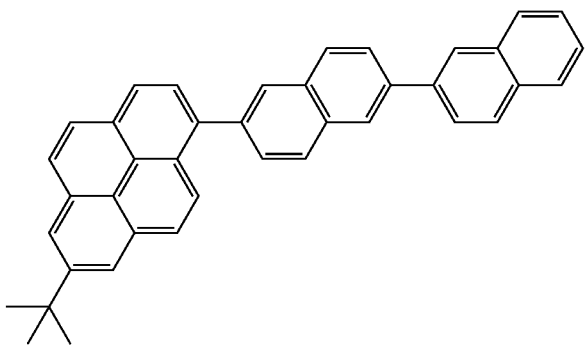 [SMILES: CC(C)(C)c1cc2ccc3ccc(-c4ccc5cc(-c6ccc7ccccc7c6)ccc5c4)c4ccc(c1)c2c34]
H4
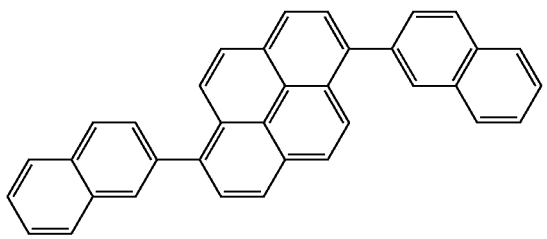 [SMILES: c1ccc2cc(-c3ccc4ccc5c(-c6ccc7ccccc7c6)ccc6ccc3c4c65)ccc2c1]
H5
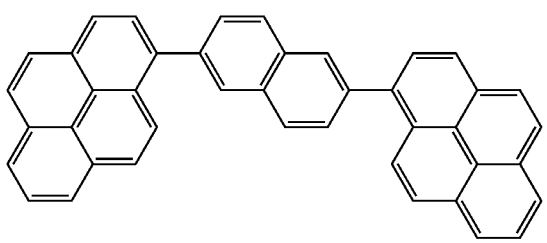 [SMILES: c1cc2ccc3ccc(-c4ccc5cc(-c6ccc7ccc8cccc9ccc6c7c89)ccc5c4)c4ccc(c1)c2c34]
H6

TABLE 2-continued
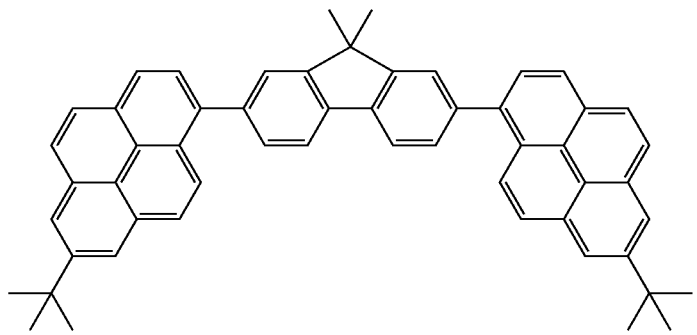 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H7
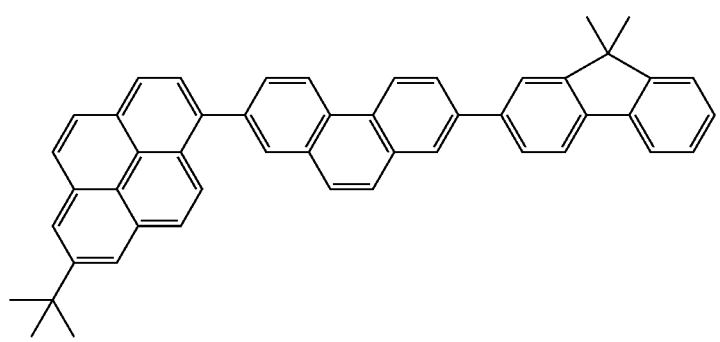 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H8
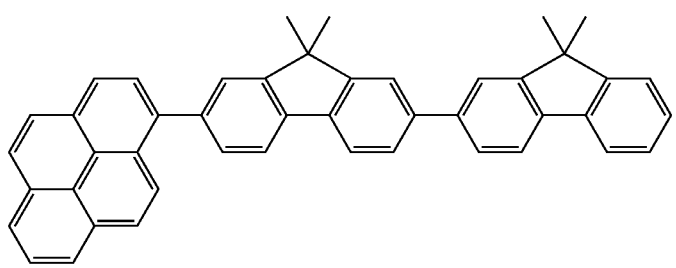 [SMILES: CC1(C)c2ccccc2-c2ccc(-c3ccc4c(c3)C(C)(C)c3cc(-c5ccc6ccc7cccc8ccc5c6c78)ccc3-4)cc21]
H9
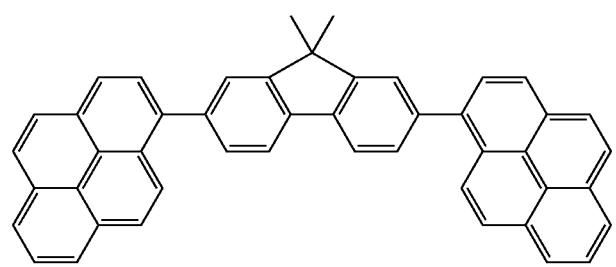 [SMILES: CC1(C)c2cc(-c3ccc4ccc5cccc6ccc3c4c56)ccc2-c2ccc(-c3ccc4ccc5cccc6ccc3c4c56)cc21]
H10
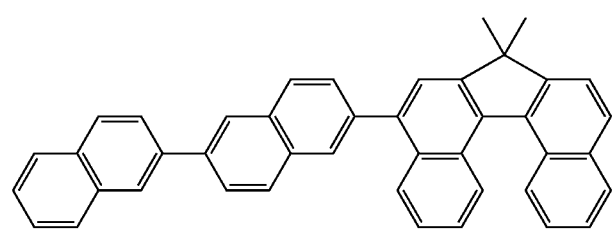 [SMILES: CC1(C)c2ccc3ccccc3c2-c2c1cc(-c1ccc3cc(-c4ccc5ccccc5c4)ccc3c1)c1ccccc21]
H11

TABLE 2-continued
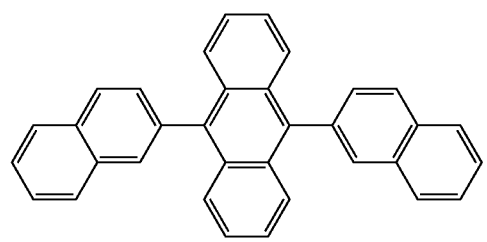 [SMILES: c1ccc2cc(-c3c4ccccc4c(-c4ccc5ccccc5c4)c4ccccc34)ccc2c1] H12
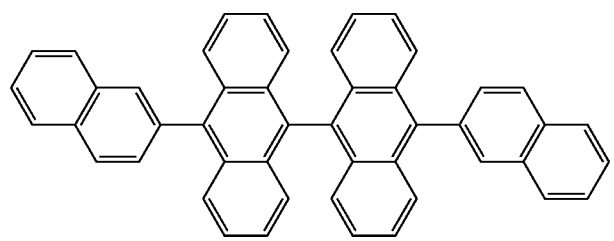 [SMILES: c1ccc2cc(-c3c4ccccc4c(-c4c5ccccc5c(-c5ccc6ccccc6c5)c5ccccc45)c4ccccc34)ccc2c1] H13
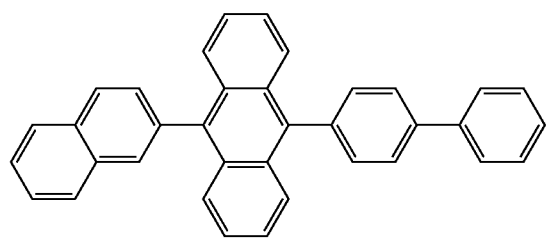 [SMILES: c1ccc(-c2ccc(-c3c4ccccc4c(-c4ccc5ccccc5c4)c4ccccc34)cc2)cc1] H14
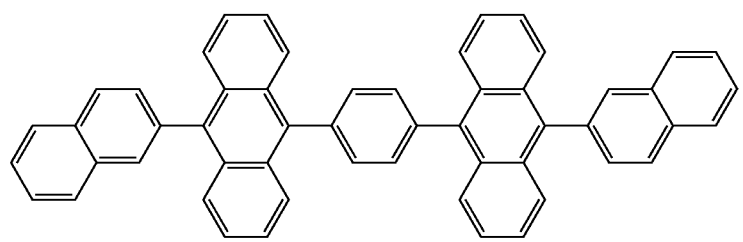 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H15
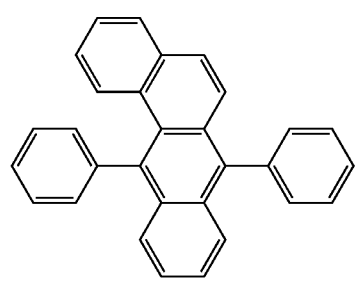 [SMILES: c1ccc(-c2c3ccccc3c(-c3ccccc3)c3c2ccc2ccccc23)cc1] H16

TABLE 2-continued
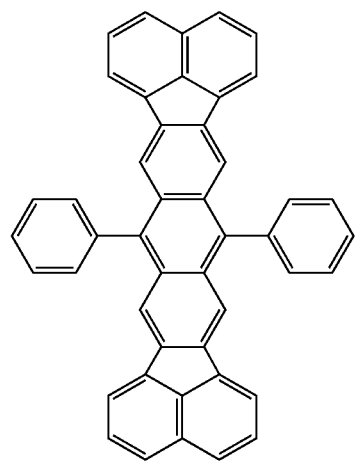 [SMILES: c1ccc(-c2c3cc4c(cc3c(-c3ccccc3)c3cc5c(cc23)-c2cccc3cccc-5c23)-c2cccc3cccc-4c23)cc1]
H17
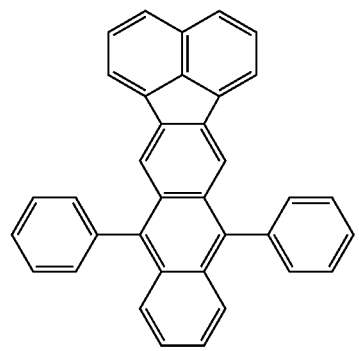 [SMILES: c1ccc(-c2c3ccccc3c(-c3ccccc3)c3cc4c(cc23)-c2cccc3cccc-4c23)cc1]
H18
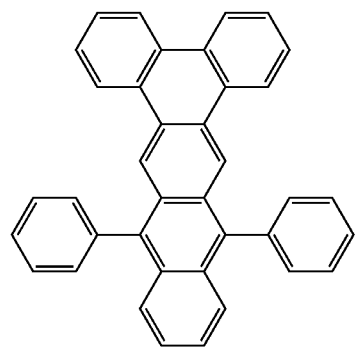 [SMILES: c1ccc(-c2c3ccccc3c(-c3ccccc3)c3cc4c5ccccc5c5ccccc5c4cc23)cc1]
H19
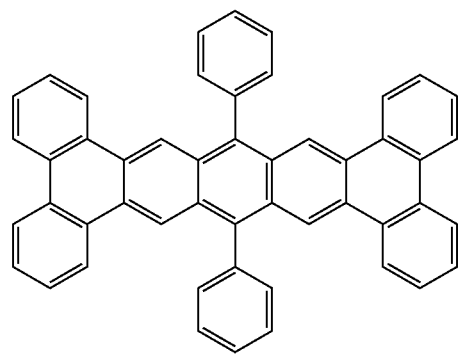 [SMILES: c1ccc(-c2c3cc4c5ccccc5c5ccccc5c4cc3c(-c3ccccc3)c3cc4c5ccccc5c5ccccc5c4cc23)cc1]
H20

TABLE 2-continued

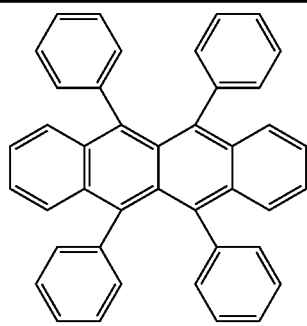

H21

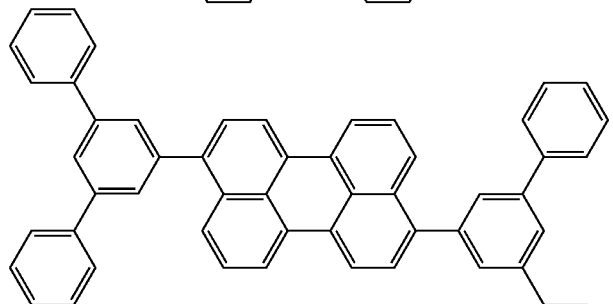

H22

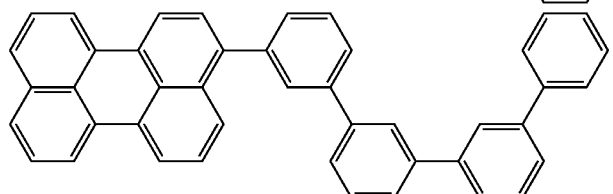

H23

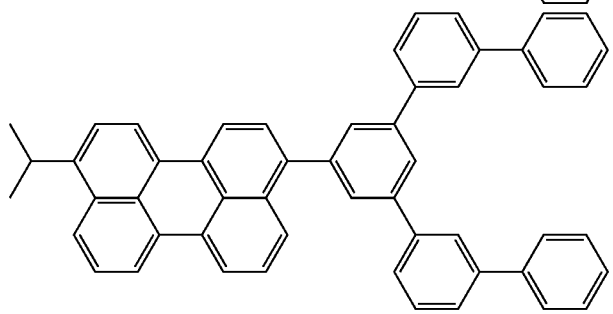

H24

The electron injectable materials or the electron transportable materials are selected considering, for example, the balance with the hole mobility of the hole injectable materials or the hole transportable materials. Mentioned as materials having electron injection performance or electron transportation performance are an oxadiazole derivative, an oxazole derivative, a pyrazine derivative, a triazole derivative, a triazine derivative, a quinoline derivative, a quinoxaline derivative, a phenanthroline derivative, an organic aluminum complex, and the like and it is a matter of course that the materials are not limited thereto.

An anode material may be a material having as high a work function as possible. For example, simple metals, such as gold, platinum, silver, copper, nickel, palladium, cobalt, selenium, vanadium, and tungsten, alloys thereof, and metal oxides, such as a tin oxide, a zinc oxide, an indium oxide, an indium tin oxide (ITO), and a zinc oxide indium are mentioned. Further, conductive polymers, such as polyaniline, polypyrrole, and polythiophene, may be acceptable. These electrode substances may be used singly or in combination of two or more kinds thereof. The anode may be a single layer structure or a multi-layer structure.

In contrast, a cathode material may be a material having a low work function. For example, alkaline metals, such as lithium, alkaline-earth metals, such as calcium, simple metals, such as aluminum, titanium, manganese, silver, lead, and chromium, are mentioned. Or, alloys containing combinations of these simple metals can also be used. For example, magnesium-silver, aluminum-lithium, aluminum-magnesium, and the like can be used. Metal oxides, such as an indium tin oxide (ITO), can also be utilized. These electrode substances may be used singly or in combination of two or more kinds thereof. The cathode may be a single layer structure or a multi-layer structure.

In the organic light-emitting device according to this embodiment, the layer containing the condensed polycyclic compound according to this embodiment and the layer containing another organic compound are formed by methods mentioned below.

For example, the layer is formed by a vacuum deposition method, an ionization vapor deposition method, a sputtering method, plasma processing or a known coating method, such as spin coating, dipping, casting, a LB method, and an ink-jet method after dissolving in a suitable solvent.

Herein, when the layer is formed by a vacuum deposition method, a solution application method, or the like, crystallization or the like is difficult to occur and the stability over time is excellent. When the layer is formed by the application methods, a film can also be formed in combination with a suitable binder resin.

Mentioned as the binder resin are polyvinyl carbazole resin, polycarbonate resin, polyester resin, ABS resin, acrylic resin, polyimide resin, phenol resin, epoxy resin, silicone resin, urea resin, and the like and the binder resin is not limited thereto.

The binder resin may be used singly as a homopolymer or a copolymer or as a mixture of two or more kinds thereof. Furthermore, known additives, such as a plasticizer, an antioxidant, and a UV absorber, may optionally be used together.

Use of Organic Light-Emitting Device According to this Embodiment

The organic light-emitting device according to this embodiment can be used for a display device or a lighting device. In addition thereto, the organic light-emitting device according to this embodiment can be used for the exposure light source of an electrophotographic image formation device, a backlight of a liquid crystal display device, and the like.

The display device has the organic light-emitting device according to this embodiment in a display portion. The display portion has a plurality of pixels. The pixels have the organic light-emitting device according to this embodiment and an active device. As an example of the active device, a switching device for controlling the light emission luminosity is mentioned. As an example of the switching device, a TFT device is mentioned. To the switching device, the anode or the cathode of the organic light-emitting device and the drain electrode or the source electrode of a thin film transistor are connected.

The display device can be used as an image display device of a PC, a head mounted display, a cellular phone, and the like. The image to be displayed may be a two-dimensional image or a three-dimensional image.

The display device may be an image output device having an image input portion which inputs an image information from an area CCD, a linear CCD, a memory card, or the like, and outputs the input image to a display device.

The image output device may be a digital camera in which an image pickup device, such as a CCD sensor, is used for the image input portion and which has an image pickup optical system.

The display device may have an input function capable of inputting by touching the output image. For example, a touch panel function and the like are mentioned.

The display device may be used for a display portion of a multifunction printer.

The organic light-emitting device according to this embodiment may be used for a lighting device. The lighting device has the organic light-emitting device according to this embodiment and an AC/DC converter circuit connected to the organic light-emitting device. The converter circuit refers to a circuit which converts an alternating voltage to a direct-current voltage.

The color of the light of the lighting device according to this embodiment may be white light, natural white light, or light of another color.

When emitting white light, the light emitting portion of the organic light-emitting device has a plurality of light-emitting layers, and the compound according to aspects of the invention emits red light and other layers emit light of colors except red color, so that white light is emitted as a device.

Figure 2:
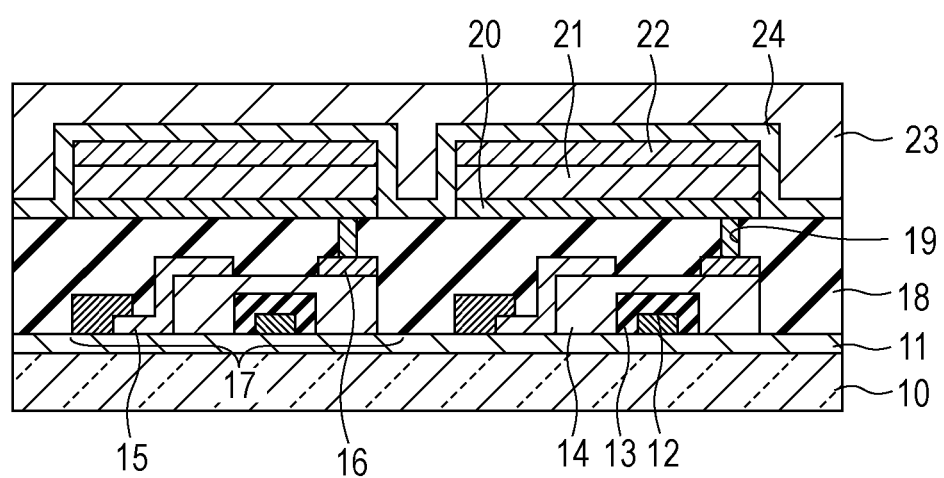
FIG. 2 is a cross-sectional schematic view illustrating the organic light-emitting device according to this embodiment and a switching device connected to the organic light-emitting device.

FIG. 2 is a cross-sectional schematic view of a display device having the organic light-emitting device according to this embodiment and a TFT device connected thereto.

The display device is provided with a substrate 10, such as glass, and a moisture barrier film 11 for protecting the TFT device or the organic compound layer on the substrate 10. The reference numeral 12 denotes a metal gate electrode 12. The reference numeral 13 denotes a gate insulation film 13. The reference numeral 14 denotes a semiconductor layer.

A TFT device 17 has the semiconductor layer 14, a drain electrode 15, and a source electrode 16. On the TFT device 17, an insulation film 18 is provided. An anode 20 of the organic light-emitting device and the source electrode 16 are connected to each other through a contact hole 19.

The display device according to this embodiment is not limited to the configuration and either one of the anode or the cathode may be connected to either one of the source electrode or the drain electrode of the TFT device.

In this drawing, an organic compound layer 21 having multiple layers is illustrated like one layer but the organic compound layer may have a multilayer structure. On the cathode 22, a first protective layer 23 and a second protective layer 24 for suppressing degradation of the organic light-emitting device are provided.

In the organic light-emitting device according to this embodiment, the light emission luminosity is controlled by the TFT device which is an example of a switching device. By providing the organic light-emitting device in a plurality of planes, an image can be displayed due to the light emission luminosity of each light-emitting device.

The switching device of the organic light-emitting device according to this embodiment is not limited to the TFT device. An aspect may be acceptable in which an active-matrix driver is formed on a transistor, an MIM device, or a substrate, such as a Si substrate, and the organic light-emitting device is provided thereon and controlled.

These configurations are selected depending on the degree of fineness, and, for example, when the degree of fineness is such that 1 inch and approximately QVGA resolution, the organic light-emitting device is suitably provided on a Si substrate.

By driving the display device employing the organic light-emitting device according to this embodiment, display with high image quality and stability over a prolonged period of time can be achieved.

The organic light-emitting device according to this embodiment may be used for an exposure light source of an image formation device. The image formation device is an image formation device having a photoconductor, an electrifying portion which electrifies the surface of the photoconductor, an exposure portion which exposes the photoconductor, and a development unit which develops an electrostatic latent image formed on the photoconductor.

The exposure light source in the image formation device refers to a light source having a plurality of light-emitting points, in which the plurality of light-emitting points are

33 disposed in a row and the quantity of light of the plurality of light-emitting points each is independently controlled.

EXAMPLES

Example 1

Synthesis of Exemplary Compound A1

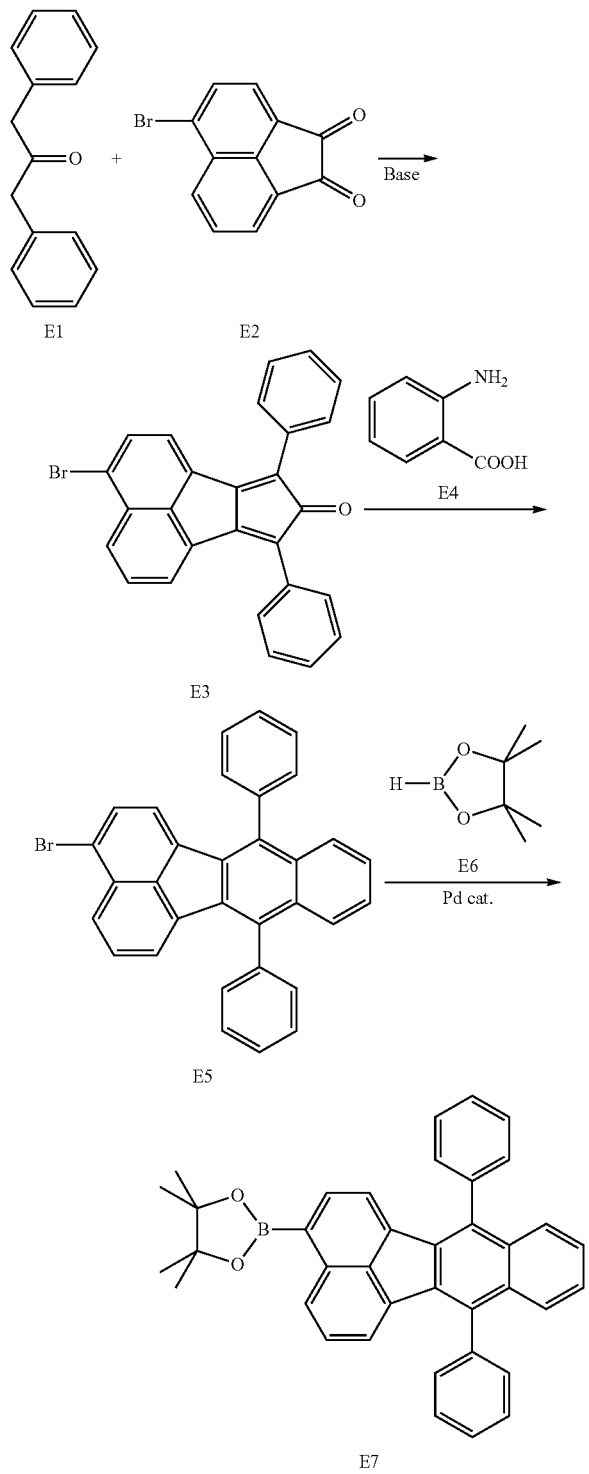

34

2.42 g (11.5 mmol) of E1 and 3.00 g (11.5 mmol) of E2 were dissolved in ethanol (40 ml), and the solution was heated to 70°. 645 mg (11.5 mmol) of potassium hydrate which was dissolved in ethanol (5 ml) was added dropwise thereto.

The solution was stirred at 70° for 3 hours. After cooling, a mixed solution of water and methanol was added, filtered, and washed with methanol. By drying the filtered substance, 4.50 g (90% yield) of a black solid E3 was obtained.

After removing a toluene (80 ml) solvent by deaeration, 4.00 g (9.19 mol) of E3 and 1.76 g (12.9 mmol) of E4 were dissolved.

1.72 ml (12.9 mmol) of isoamyl nitrite was added thereto, and the mixture was stirred at 110° for 5 hours. After cooling, the reaction solution was subjected as it was to silica gel column chromatography (mobile phase; toluene), and was condensed.

The residue was subjected to silica gel column chromatography (mobile phase; heptane:toluene=5:1), and was condensed. The resulting substance was dispersed and washed with methanol, filtered, and dried, thereby obtaining 3.78 g (85% yield) of a yellow solid E5.

A toluene (25 ml) solvent was removed by deaeration, and then 3.0 g (6.21 mmol) of E5, 1.8 ml (12.4 mmol) of E6, 435 mg (0.62 mmol) of $PdCl_2(PPh_3)_2(II)$, and 2.58 ml (18.6 mmol) of triethylamine were added, followed by stirring at 90° for 3 hours.

After cooling, methanol was added, and then filtered. The filtered substance was subjected to silica gel column chromatography (mobile phase; heptane:toluene=1:1), and was condensed. The resulting substance was dispersed and washed with methanol, filtered, and dried, thereby obtaining 2.21 g (67% yield) of a yellow solid E7.

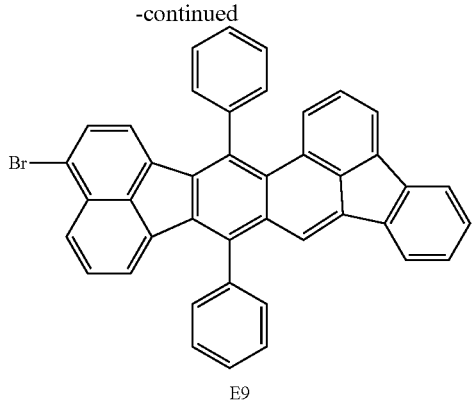

E9

A toluene (50 ml) solvent was removed by deaeration, and then 1.39 g (3.19 mol) of E3 and 1.0 g (3.83 mmol) of E8 were dissolved. 0.55 ml (4.15 mmol) of isoamyl nitrite was added thereto, and stirred at 110° for 4 hours.

After cooling, the reaction solution was subjected as it was to silica gel column chromatography (mobile phase; toluene), and was condensed. The residue was subjected to silica gel column chromatography (mobile phase; heptane:toluene=3:1), and was condensed.

The resulting substance was dispersed and washed with methanol, filtered, and dried, thereby obtaining 1.7 g (88% yield) of a yellow solid E9.

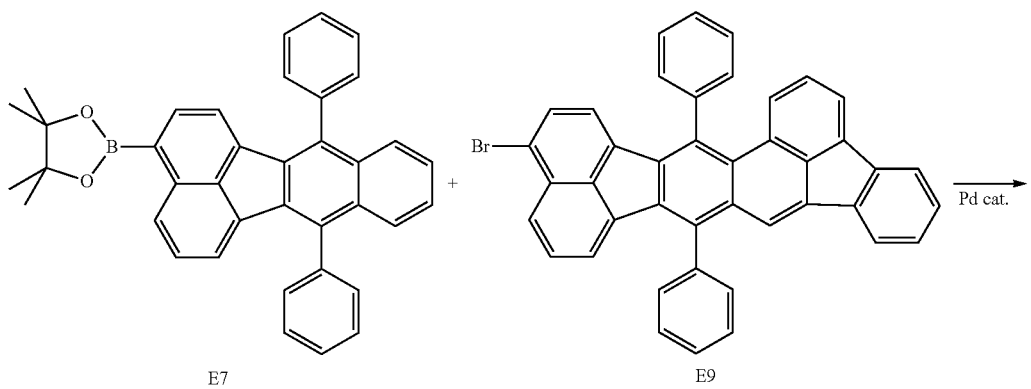

E7 + E9 → Pd cat.

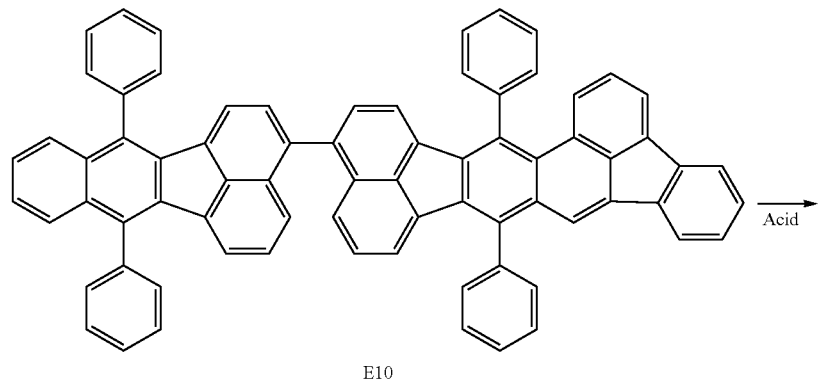

E10 → Acid

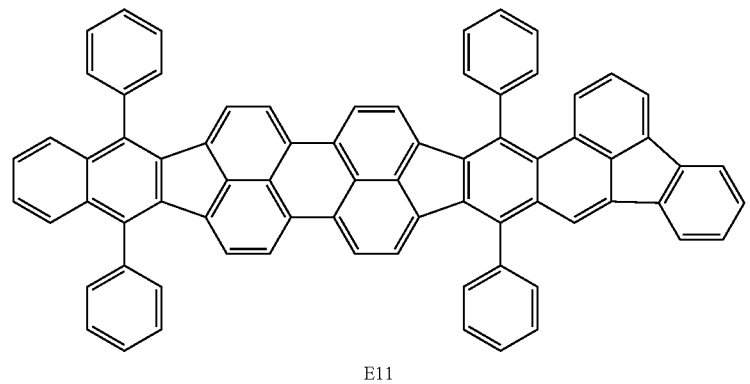

E11

A mixed solvent of toluene (16 ml), ethanol (8 ml), and an aqueous 20% sodium carbonate solution was removed by deaeration, 960 mg (1.81 mmol) of E7, 1.0 g (1.65 mmol) of E9, and 114 mg (0.1 mmol) of Pd(PPh$_3$)$_4$(0) were added, and then stirred at 90° for 4 hours.

After cooling, the resulting substance was extracted with toluene, followed by drying over sodium sulfate. After concentration, the resulting substance was subjected to silica gel column chromatography (mobile phase; heptane:chloroform=3:1), and then re-crystallized with toluene and ethanol. After filtration, by drying the same, 830 mg (54% yield) of a yellow solid E10 was obtained.

830 mg (0.16 mmol) of E10 was dissolved in dichloromethane (5 ml), and trifluoroacetic acid (1 ml) and 0.1 ml (0.81 mmol) of boron trifluoride diethyl etherate were added thereto at room temperature.

To the solution, 73 mg (0.32 mmol) of DDQ was added at room temperature, and then the mixture was stirred for 2 hours. Thereafter, 60 mg (0.32 mmol) of ferrocene was added, followed by stirring at room temperature for 1 hour. Thereafter, methanol was added for filtration, and then the filtered substance was refined by silica gel column chromatography (mobile phase; chloroform).

After concentration, the resulting substance was dispersed and washed with methanol, thereby obtaining 126 mg (84% yield) of a purple solid E11 (Exemplary Compound A1).

929 which is M+ of E11 (Exemplary Compound A1) was confirmed by mass spectrometry.

When the exemplary compound A1 was measured for the emission spectrum at room temperature in the toluene diluted solution, the maximum light emission wavelength was 606 nm. As the device, a spectrophotometer U-3010 manufactured by Hitachi, Ltd. was used.

Example 2

Synthesis of Exemplary Compound A2

An exemplary compound A2 was synthesized in the same manner as in Example 1, except changing the compound E1 to compounds E12 and E13 shown below.

1097 which is M+ of the exemplary compound A2 was confirmed by mass spectrometry.

When the exemplary compound A2 was measured for the emission spectrum at room temperature in the toluene diluted solution, the maximum light emission wavelength was 610 nm. As the device, a spectrophotometer U-3010 manufactured by Hitachi, Ltd. was used.

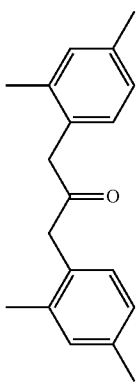

E12

-continued

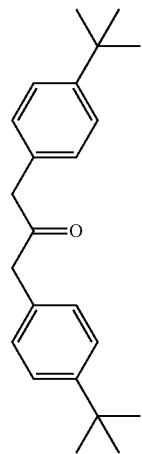

E13

Example 3

Synthesis of Exemplary Compound B1

An exemplary compound B1 was synthesized in the same manner as in Example 1, except changing the compound E1 to a compound E14 and the compound E2 to a compound E15 shown below.

877 which is M+ of the exemplary compound B1 was confirmed by mass spectrometry.

When the exemplary compound B1 was measured for the emission spectrum at room temperature in the toluene diluted solution similarly as in Example 1, the maximum light emission wavelength was 613 nm.

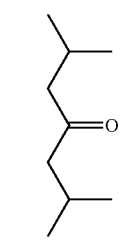

E14

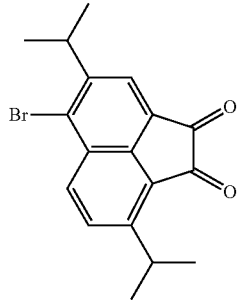

E15

Example 4

Synthesis of Exemplary Compound B4

An exemplary compound B4 was synthesized in the same manner as in Example 1, except changing the compound E1 to the compound E14 and a compound E16 and the compound E2 to the compound E15 and a compound E17 shown below.

849 which is M+ of the exemplary compound B4 was confirmed by mass spectrometry.

When the exemplary compound B4 was measured for the emission spectrum at room temperature in the toluene diluted solution similarly as in Example 1, the maximum light emission wavelength was 615 nm.

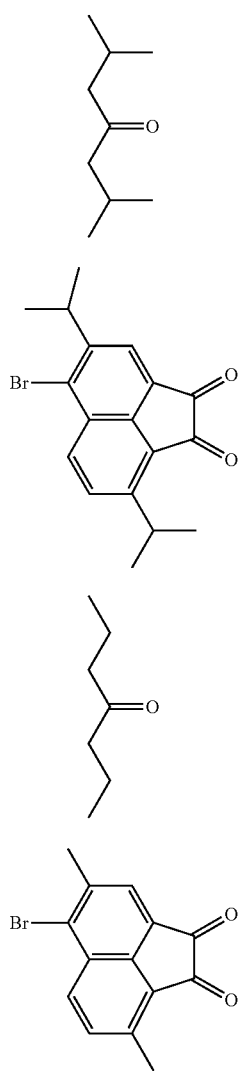

Example 5

Synthesis of Exemplary Compound C2

An exemplary compound C2 was synthesized in the same manner as in Example 1, except changing the compound E1 to the compound E14 and a compound E18 shown below.

1086 which is M+ of the exemplary compound C2 was confirmed by mass spectrometry.

When the exemplary compound C2 was measured for the emission spectrum at room temperature in the toluene diluted solution similarly as in Example 1, the maximum light emission wavelength was 608 nm.

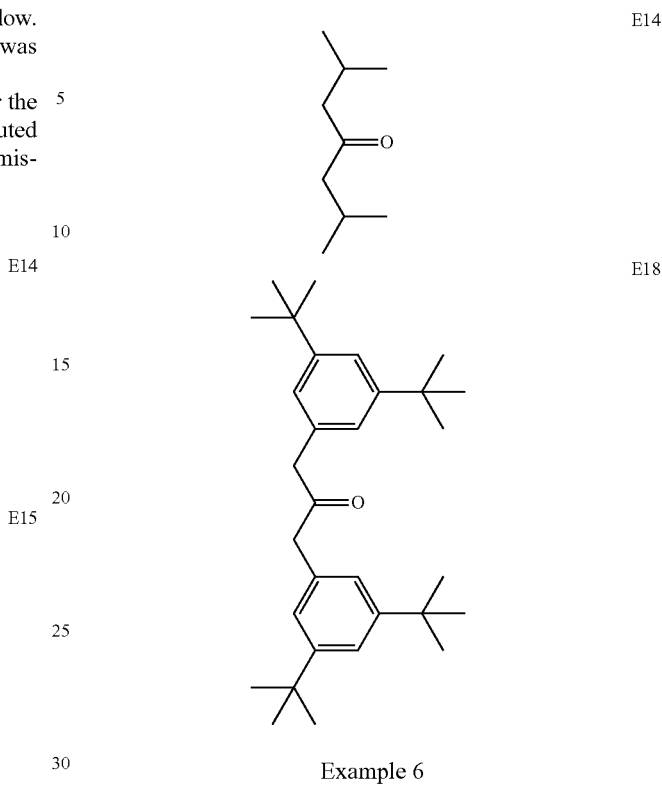

Example 6

Synthesis of Exemplary Compound C8

An exemplary compound C8 was synthesized in the same manner as in Example 1, except changing the compound E1 to the compounds E14 and E18 and the compound 2 to the compound 15 shown below.

1170 which is M+ of the exemplary compound C8 was confirmed by mass spectrometry.

When the exemplary compound C8 was measured for the emission spectrum at room temperature in the toluene diluted solution similarly as in Example 1, the maximum light emission wavelength was 617 nm.

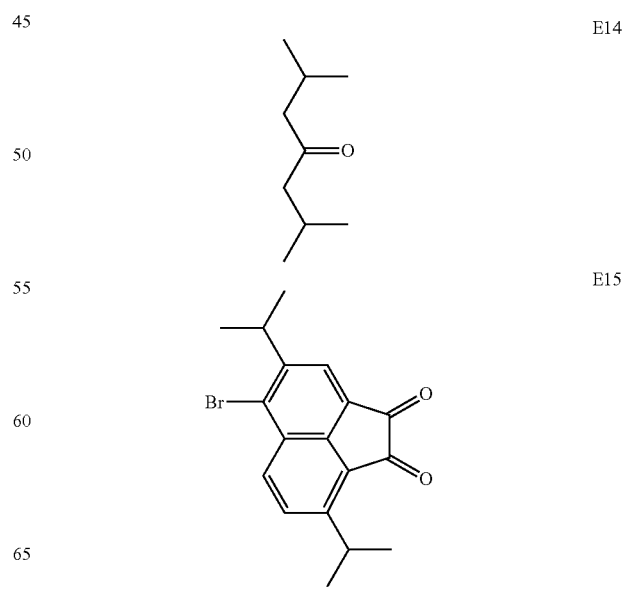

-continued

E18

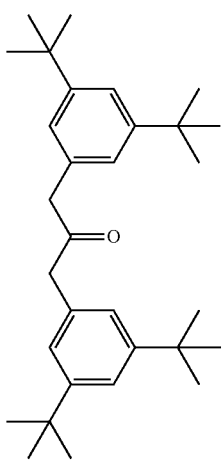

Example 7
Synthesis of Exemplary Compound D2

An exemplary compound D2 was synthesized in the same manner as in Example 1, except changing the compound E1 to the compound E14 and a compound E19 shown below.

897 which is M+ of the exemplary compound D2 was confirmed by mass spectrometry.

When the exemplary compound D2 was measured for the emission spectrum at room temperature in the toluene diluted solution similarly as in Example 1, the maximum light emission wavelength was 608 nm.

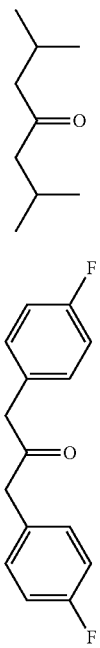

E14

E19

Example 8

In this example, an organic light-emitting device having a configuration such that an anode/a hole injecting layer/a hole transporting layer/a light-emitting layer/an electron transporting layer/an electron injecting layer/a cathode were provided in order on a substrate was produced by a method described below.

A substance obtained by forming ITO into a film with a film thickness of 120 nm as an anode by a sputtering method on a glass substrate was used as a transparent conductive support substrate (ITO substrate).

On the ITO substrate, an organic compound layer and an electrode layer described below were continuously formed by vacuum deposition utilizing resistance heating in a $10^{-5}$ Pa vacuum chamber. In this case, the organic light-emitting device was produced in such a manner that the facing electrode area was 3 mm$^2$.

Hole injecting layer (30 nm) F1
Hole transporting layer (10 nm)—F2
Light-emitting layer (30 nm) Host F3 (Weight ratio 99.5%), Guest: A1 (Weight ratio 0.5%)
Electron transporting layer (30 nm) F4
Electron injecting layer (1 nm) LiF
Metal electrode layer (100 nm) Al

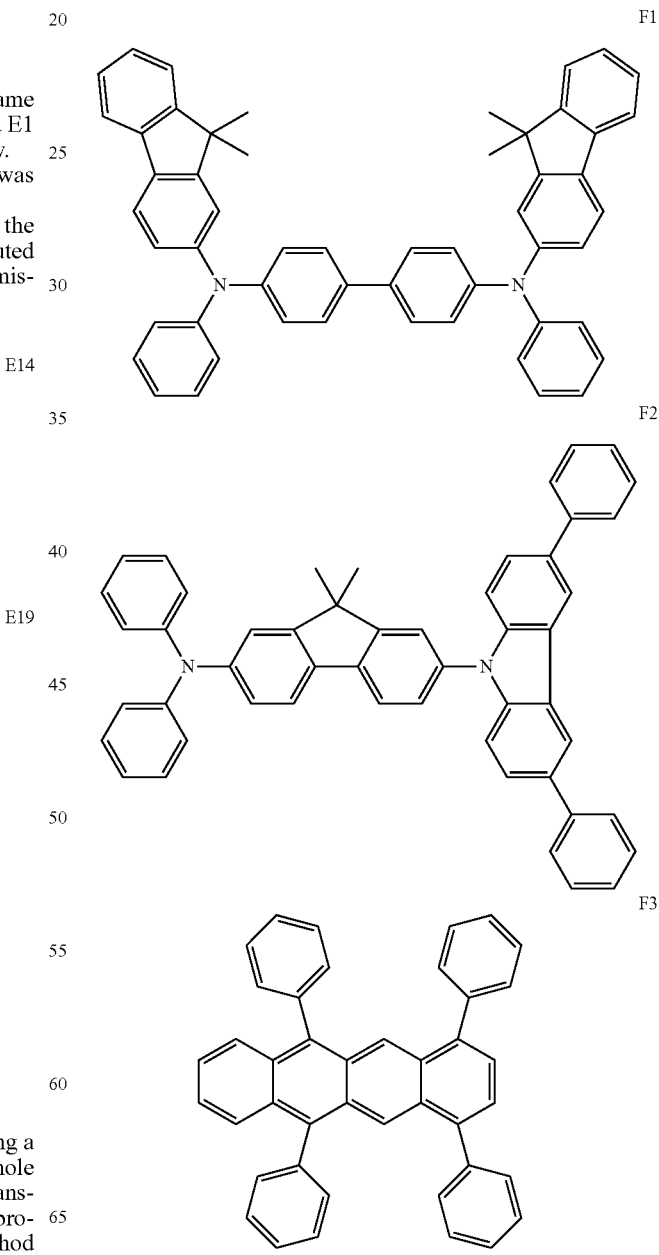

F4

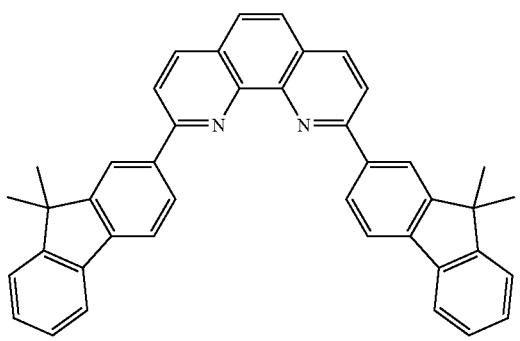

When a voltage was applied to the obtained organic light-emitting device using the ITO electrode as the anode and the Al electrode as the cathode, red light emission with luminous efficiency at a voltage of 4.6 V of 9.5 cd/A and C.I.E. chromaticity coordinates of (0.68, 0.30) was observed.

When the organic light-emitting device was driven at the initial luminance of 4500 cd/m², a degradation of the luminance was lower than 10% even when 1000 hours passed.

Example 9

An organic light-emitting device was produced in the same manner as in Example 8, except changing A1 as the guest to C2.

When a voltage was applied to the obtained organic light-emitting device using the ITO electrode as the anode and the Al electrode as the cathode, red light emission with luminous efficiency at a voltage of 4.6 V of 10.1 cd/A and C.I.E. chromaticity coordinates of (0.68, 0.31) was observed.

When the organic light-emitting device was driven at the initial luminance of 4500 cd/m², a degradation of the luminance was lower than 10% even when 1000 hours passed.

Example 10

An organic light-emitting device was produced in the same manner as in Example 8, except changing A1 as the guest to D2.

When a voltage was applied to the obtained organic light-emitting device using the ITO electrode as the anode and the Al electrode as the cathode, red light emission with luminous efficiency at a voltage of 4.6 V of 11.5 cd/A and C.I.E. chromaticity coordinates of (0.68, 0.31) was observed.

When the organic light-emitting device was driven at the initial luminance of 4500 cd/m², a degradation of the luminance was lower than 10% even when 500 hours passed.

Example 11

In this example, a white organic light-emitting device having a configuration such that an anode/a hole injecting layer/a hole transporting layer/a red light-emitting layer/a green light-emitting layer/a blue light-emitting layer/an electron transporting layer an electron injecting layer/a cathode were provided in order on a substrate was produced by a method described below.

A substance obtained by forming ITO into a film with a film thickness of 120 nm as an anode by a sputtering method on a glass substrate was used as a transparent conductive support substrate (ITO substrate).

On the ITO substrate, an organic compound layer and an electrode layer described below were continuously formed by vacuum deposition utilizing resistance heating in a $10^{-5}$ Pa vacuum chamber. In this case, the organic light-emitting device was produced in such a manner that the facing electrode area was 3 mm².

Hole injecting layer (30 nm) G1
Hole transporting layer (10 nm) G2
Red light-emitting layer (15 nm) Host 1 G5 (Weight ratio 98.5%), Host 2 G7 (Weight ratio 1.0%), and Guest: C2 (Weight ratio 0.5%)
Green light-emitting layer (5 nm) Host G5 (Weight ratio 95.0%) and Guest: G7 (Weight ratio 5.0%)
Blue light-emitting layer (20 nm) Host G5 (Weight ratio 95.0%) and Guest: G6 (Weight ratio 5.0%)
Electron transporting layer (30 nm) G4
Electron injecting layer (1 nm) LiF
Metal electrode layer (100 nm) Al

G5

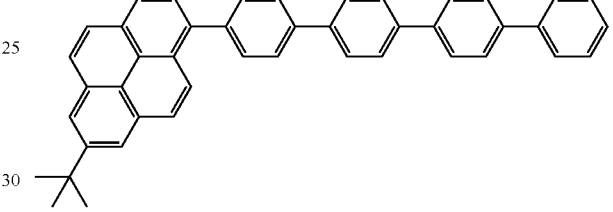

G7

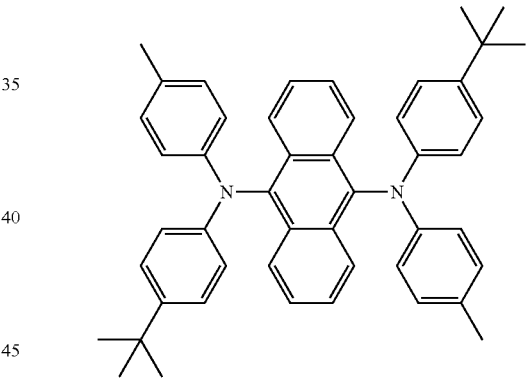

G6

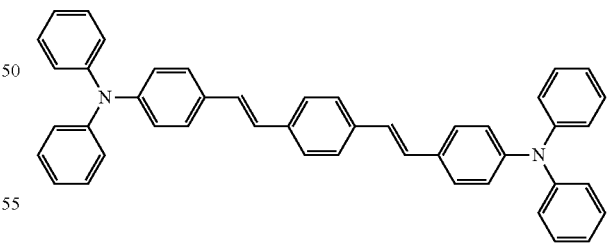

When a voltage was applied to the obtained organic light-emitting device using the ITO electrode as the anode and the Al electrode as the cathode, white light emission with C.I.E. chromaticity coordinates of (0.32, 0.35) was observed.

Example 12

An organic light-emitting device was produced in the same manner as in Example 11, except changing C1 as the guest to D2.

When a voltage was applied to the obtained organic light-emitting device using the ITO electrode as the anode and the Al electrode as the cathode, white light emission with C.I.E. chromaticity coordinates of (0.32, 0.35) was observed.

Results and Consideration

As described above, the novel condensed polycyclic compound according to aspects of the invention can provide a red organic light-emitting device which emits red light, has high color purity and has high efficiency.

Moreover, a white light-emitting device can be provided by combining light-emitting materials of other light emission colors.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-186205 filed Aug. 29, 2011, which is hereby incorporated by reference herein in its entirety.

What is claimed is:

1. A condensed polycyclic compound represented by the following general formula [1],

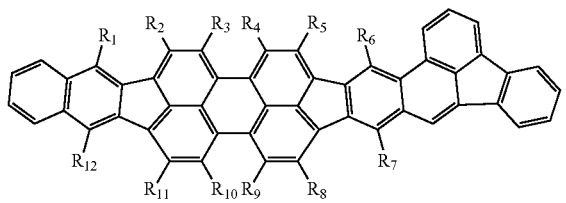

[1]

wherein, in General Formula [1],
$R_1$, $R_6$, $R_7$, and $R_{12}$ each are independently selected from a hydrogen atom, an alkyl group, or an aryl group,
the aryl group may have an alkyl group and a fluorine atom as a substituent, and
$R_2$ to $R_5$ and $R_8$ to $R_{11}$ each are independently selected from a hydrogen atom and an alkyl group.

2. An organic light-emitting device comprising:
a pair of electrodes; and
an organic compound layer disposed between the pair of electrodes, wherein
the organic compound layer has the condensed polycyclic compound according to claim 1.

3. The organic light-emitting device according to claim 2, wherein the organic compound layer is a light-emitting layer.

4. The organic light-emitting device according to claim 3, which emits red light.

5. The organic light-emitting device according to claim 2, which emits white light, wherein
the organic compound layer has a plurality of light-emitting layers,
at least one of the plurality of light-emitting layers has the condensed polycyclic compound, and
the plurality of light-emitting layers each are light-emitting layers which emit lights of different colors.

6. The organic light-emitting device according to claim 2, wherein
the organic compound layer has a plurality of light-emitting layers,
the light-emitting layer having the condensed polycyclic compound among the plurality of light-emitting layers is a light-emitting layer which emits red light, and
white light is emitted by mixing colors of lights emitted from the light-emitting layers other than the light-emitting layer which emits red light and the red light.

7. A display device comprising:
a plurality of pixels, wherein
at least one of the plurality of pixels has the organic light-emitting device according to claim 2 and an active device connected to the organic light-emitting device.

8. An image information processing device comprising:
an input portion for inputting an image information; and
a display portion for displaying an image, wherein
the display portion is the display device according to claim 7.

9. A lighting device, comprising:
the organic light-emitting device according to claim 2; and
an AC/DC converter circuit which supplies a drive voltage to the organic light-emitting device.

10. An image formation device comprising:
a photoconductor;
an electrifying portion which electrifies the surface of the photoconductor;
an exposure portion which exposes the photoconductor; and
a development unit which develops an electrostatic latent image formed on the photoconductor, wherein
the exposure portion has the organic light-emitting device according to claim 2.

11. An exposure light source for exposing a photoconductor comprising:
a plurality of light-emitting points, wherein
the plurality of light-emitting points are disposed in a row,
the quantity of light of the plurality of light-emitting points each is independently controlled, and
the plurality of light-emitting points have the organic light-emitting device according to claim 2.

* * * * *